(12) United States Patent
Farquharson et al.

(10) Patent No.: US 6,623,977 B1
(45) Date of Patent: Sep. 23, 2003

(54) MATERIAL FOR SURFACE-ENHANCED RAMAN SPECTROSCOPY, AND SER SENSORS AND METHOD FOR PREPARING SAME

(75) Inventors: Stuart Farquharson, Meriden, CT (US); Chad Nelson, Windsor, CT (US); Yuan-Hsiang Lee, Holyoke, MA (US)

(73) Assignee: Real-Time Analyzers, Inc., East Hartford, CT (US)

( * ) Notice: Subject to any disclaimer, the term of this patent is extended or adjusted under 35 U.S.C. 154(b) by 468 days.

(21) Appl. No.: 09/704,818

(22) Filed: Nov. 2, 2000

Related U.S. Application Data
(60) Provisional application No. 60/164,030, filed on Nov. 5, 1999.

(51) Int. Cl.[7] .............................................. G01N 21/65
(52) U.S. Cl. ..................... 436/164; 436/171; 422/82.05; 356/301
(58) Field of Search ........................ 356/301; 422/82.05, 422/82.09, 82.11; 436/164, 171; 427/164, 165

(56) References Cited

U.S. PATENT DOCUMENTS

| | | | | |
|---|---|---|---|---|
| 5,017,007 A | * | 5/1991 | Milne et al. ................. | 356/301 |
| 5,255,067 A | * | 10/1993 | Carrabba et al. ............ | 356/301 |
| 5,445,972 A | * | 8/1995 | Tarcha et al. ................ | 436/544 |
| 5,527,712 A | * | 6/1996 | Sheehy ......................... | 436/525 |
| 6,514,767 B1 | * | 2/2003 | Natan .......................... | 436/166 |
| 2003/0029274 A1 | * | 2/2003 | Natan et al. ................. | 356/301 |

FOREIGN PATENT DOCUMENTS

| | | | |
|---|---|---|---|
| WO | WO 01/33189 | * | 5/2001 |
| WO | WO 03/010511 | * | 2/2003 |

OTHER PUBLICATIONS

Murphy, T. "Use of sol–gel techniques in the development of surface–enhanced Raman scattering (SERS) substrates suitable for in situ detection of chemicals in sea–water" Appl. Phys. B, vol. 69, pp. 147–150 (Jul. 07, 1999).*

Akbarian, F. et al "Surface–Enhanced Raman Spectroscopy Using Photodeposited Gold Particles in Porous Sol–Gel Silicates" J. Phys. Chem. vol. 99, pp. 3892–3894 (1995).*

"Silver–Doped Sol–Gel Films as the Substrate for Surface–Enhanced Raman Scattering," Lee, Y.H. et al. J. Raman Spectrosc., 28 635–639 (1997).

* cited by examiner

*Primary Examiner*—Jeffrey Snay
(74) *Attorney, Agent, or Firm*—Ira S. Dorman (57) ABSTRACT

Metal-doped sol-gel materials, suitable for use as sensors for surface-enhanced Raman spectroscopic analysis for trace chemical detection, are produced by effecting gelation and solvent removal of a doped sol-gel under mild temperature conditions. At least in certain instances reaction and drying will desirably be effected in an oxygen-starved environment. The metal of the sol-gel material functions, when irradiated, to produce a plasmon field for interaction with molecules of an analyte in contact therewith, increasing by orders of magnitude Raman photons that are generate by excitation radiation, and the method allows matching of the metal and metal particle size to a wavelength of light (or incident radiation, e.g., laser radiation) to generate surface plasmons. The porosity of the sol-gel material dramatically increases the surface area, and thereby the amount of metal exposed for analyte interaction. The sensors provided may be in the form of glass vials, fiber optics, multi-well micro-sample plates, etc., having surface coatings of the doped sol-gel material, to provide sampling systems for use in a Raman instrument.

22 Claims, 5 Drawing Sheets

MATERIAL FOR SURFACE-ENHANCED RAMAN SPECTROSCOPY, AND SER SENSORS AND METHOD FOR PREPARING SAME

CROSS-REFERENCE TO RELATED APPLICATION

The present application claims the benefit of U.S. Provisional Application No. 60/164,030, filed Nov. 5, 1999 in the names of the present inventors.

STATEMENT REGARDING FEDERALLY SPONSORED RESEARCH OR DEVELOPED

The United States Government has rights in this invention pursuant to NASA Contract No. NAS9-98024.

BACKGROUND OF THE INVENTION

The ability to detect and identify trace quantities of chemicals has become increasingly important in virtually every scientific discipline, ranging from part per billion analyses of pollutants in sub-surface water to analysis of cancer treatment drugs in blood serum. Surface-enhanced Raman spectroscopy (SERS) has proven to be one of the most sensitive methods for performing such chemical analyses by the detection of a single molecule (see Nie, S. and S. R. Emory, "Probing Single Molecules and Single Nanoparticles by Surface Enhanced Raman Scattering", Science, 275,1102 (1997)). A Raman spectrum, similar to an infrared spectrum, consists of a wavelength distribution of bands corresponding to molecular vibrations specific to the sample being analyzed (the analyte). For example, appended FIG. 3 (to be discussed more fully below) shows the infrared and Raman spectra of adenine. In the practice of Raman spectroscopy, the beam from a light source, generally a laser, is focused upon the sample to thereby generate inelastically scattered radiation, which is optically collected and directed into a wavelength-dispersive spectrometer in which a detector converts the energy of impinging photons to electrical signal intensity.

Historically, the very low conversion of incident radiation to inelastic scattered radiation limited Raman spectroscopy to applications that were difficult to perform by infrared spectroscopy, such as the analysis of aqueous solutions. It was discovered in 1974 however that when a molecule in close proximity to a roughened silver electrode is subjected to a Raman excitation source the intensity of the signal generated is increased by as much as six orders of magnitude. (see Fleischmann, M., Hendra, P. J., and McQuillan, A. J., "Raman Spectra of Pyridine Adsorbed at a Silver Electrode," Chem. Phys. Lett, 26, 123, (1974), and Weaver, M. J., Farquharson, S., Tadayyoni, M. A., "Surface-enhancement factors for Raman scattering at silver electrodes. Role of adsorbate-surface interactions and electrode structure," J. Chem. Phys., 82, 4867–4874 (1985)). The mechanism responsible for this large increase in scattering efficiency has been the subject of considerable research (see Section Four: Theory in "Surface-Enhanced Raman Scattering," [M. Kerker and B. Thompson Eds.] SPIE, MS 10, also p. 225 (1990)). A description of the theory is given by B. Pettinger in "Light Scattering by Adsorbates at Ag Particles; Quantum-Mechanical Approach for Energy Transfer Induced Interfacial Optical Processes Involving Surface Plasmons, Multipoles, and Electron-hole Pairs," J. Chem. Phys., 85, 7442–7451 (1986). Briefly, incident laser photons couple to free conducting electrons within the metal which, confined by the particle surface, collectively cause the electron cloud to resonate. The resulting surface plasmon field provides an efficient pathway for the transfer of energy to the molecular vibrational modes of a molecule within the field, and thus generates Raman photons (see "Surface-Enhanced Raman Scattering; Section Four: Theory", supra).

Figure 3:
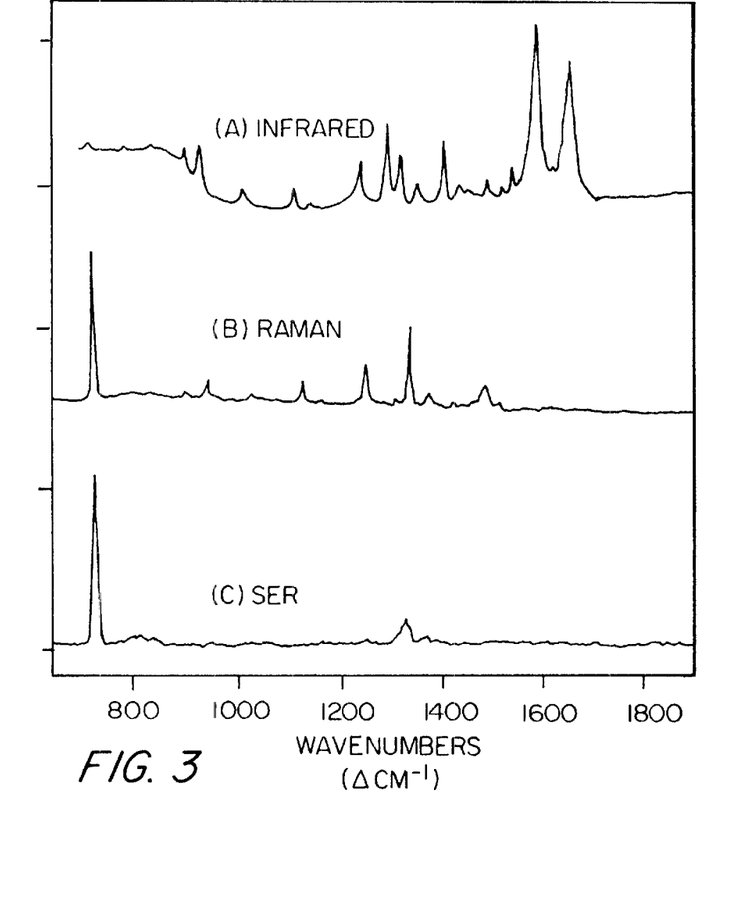
FIG. 3 is a plot of curves showing (A) infrared, (B) Raman, and (C) surface-enhanced Raman spectra of adenine.

The described phenomenon occurs however only if the following three conditions are satisfied: (1) that the free-electron absorption of the metal can be excited by light of wavelength between 250 and 2500 nanometers (nm), preferably in the form of laser beams; (2) that the metal employed is of the appropriate size (normally 5 to 1000 nm diameter particles, or a surface of equivalent morphology), and has optical properties necessary for generating a surface plasmon field; and (3) that the analyte molecule has effectively matching optical properties (absorption) for coupling to the plasmon field (see Weaver, J. Chem. Phys., 82, 4867–4874 (1985), and Pettinger, J. Chem. Phys., 85, 7442–7451 (1986), supra). Although limited signal enhancement has been observed for the other coinage metals, such as nickel and platinum, as well as for alloys containing one or more of the coinage metals, as a practical matter the foregoing conditions restrict SERS to the Periodic Table Group IB metals, copper, gold, and silver, with diameters between 5 and 200 nm (see Pettinger, J. Chem. Phys, 85, 7442–7451 (1986) supra, and Wang, D. -S., and Kerker, M., "Enhanced Raman Scattering by Molecules Adsorbed at the Surface of Colloidal Spheroids," Physical Review B., 24, 1777–1790 (1981)). The SERS method has been used to measure the spectra of adenine on a silver-doped sol-gel coated glass substrate, and has achieved signal increases of six orders of magnitude, as shown by appended FIG. 3(c).

Analyses for numerous chemicals and biochemical by SERS has been demonstrated using: (1) activated electrodes in electrolytic cells (see Lombardi, D. R., C. Wang, B. Sun, A. W. Fountain III, T. J. Vickers, C. K. Mann, F. R. Reich, J. G. Douglas, B. A. Crawford, and F. L. Kohlasch, Appl. Spectrosc. 48, 875–833 (1994); Storey, J. M. E., Shelton, R. D., Barber, T. E., and Wachter, E. A., "Electrochemical SERS Detection of Chlorinated Hydrocarbons in Aqueous Solutions," Appl. Spectrosc., 48, 1265–1271 (1994); Freeman, R. D., Hammaker, R. M., Meloan, C. E., and Fately, W. G., "A detector for liquid chromatography and flow injection analysis using SERS," Appl. Spectrosc., 42, 456–460 (1988); Angel, S. M., L. F. Katz, D. D. Archibold, L. T. Lin, D. E. Honigs, App. Spectrosc. 42, 1327 (1988); and Vo-Dinh, T., Stokes, D. L., Li, Y. S., and Miller, G. H., "Fiber-Optic Sensor Probe For In-Situ Surface-Enhanced Raman Monitoring," SPIE, 1368, 203–209 (1990)); (2) activated silver and gold colloid reagents (see Berthod, A., J. J. Laserna, and J. D. Winefordner, "SERS on silver hydrosols studied by flow injection analysis", Appl. Spectrosc. 41, 1137–1141 (1987) 42, 456–460 (1988) and Angel, S. M., L. F. Katz, D. D. Archibold, L. T. Lin, D. E. Honigs, Appl. Spectrosc. 42, 1327 (1988); and (3) activated silver and gold substrates (see Vo-Dinh, SPIE, 1368, 203–209 (1990), and Storey, J. M. E. Barber, T. E., Shelton, R. D., Wacher, E. A., Carron, K. T., and Jiang, Y. "Applications of Surface-Enhanced Raman Scattering (SERS) to Chemical Detection", Spectroscopy, 10(3), 20–25 (1995). None of the foregoing techniques is capable of providing quantitative measurements, however, and consequently SERS has not gained widespread use.

More specifically, the first technique referred to uses electrodes that are "roughened" by changing the applied potential between oxidation and reduction states; it is found that the desired metal surface features (roughness) cannot be reproduced faithfully from one procedure to the next, and the method is also limited to electrolyte solutions. In the second technique, colloids are prepared by reducing a metal salt solution to produce metal particles, which in turn form aggregates. Particle size and aggregate size are strongly influenced by initial chemical concentrations, temperature, pH, and rate of mixing, and again therefore the desired features are not reproducible; also, the method is limited to aqueous solutions. Finally, the third technique mentioned uses substrates that are prepared by depositing the desired metal onto a surface having the appropriate roughness characteristics. To permit the analysis, the sample is preferably dried on the surface to concentrate the analyte on the active metal, and once again replication is difficult to achieve; the colloids and substrates are further limited moreover in that the chemical interaction of the analyte and the SER-active metal is not reversible, thus precluding use of the materials for repeat measurements. The relative merits of the three methods described above, for preparing SER-active surfaces, have been further reviewed by K. L. Norrod, L. M. Sudnik, D. Rousell, and K. L. Rowlen in "Quantitative comparison of five SERS substrates: Sensitivity and detection limit," *Appl. Spectrosc.*, 51, 994–1001 (1997).

SUMMARY OF THE INVENTION

It is therefore the broad object of the present invention to provide a novel method for preparing a SERS-active material that, in general, avoids the deficiencies of the techniques heretofore known and that enables reproducible, reversible, and quantitative measurements to be performed with a high level of accuracy.

A more specific object of the invention is to provide a novel method for incorporating metal particles within a sol-gel matrix so as to produce a SERS-active material having the foregoing features and advantages.

Other more specific objects of the invention are to provide a novel SERS-active material that is not restricted to specific environments, such as electrolytes, particular solvents, or as evaporates on surfaces, and to provide a method for the preparation thereof.

A further object of the invention is to provide novel sample holders (e.g. internally coated vials and multiple-well micro-sample plates) sampling systems (e.g., internally coated tubing for sample flow), and sample probes (e.g., externally coated rods or fiber optics that can be placed into a sample), suitable for use in performing SERS analyses.

Yet another object of the invention is to provide a novel chemical analysis technique using surface-enhanced Raman spectroscopy and, in particular, such an analysis technique that employs the sample holders, systems, and probes fabricated in accordance herewith.

The foregoing and related objects of the invention are achieved, in general, by providing a chemical synthesis route for incorporating a metal within a sol-gel, such that interactions between impinging radiation and analyte molecules at the surface of the metal within the prepared sol-gel are enhanced, so as to in turn enhance the efficiency with which inelastically scattered (Raman) photons are generated. The chemical route described provides a means for optimally selecting the metal particle, the size of the particles, and the concentration of the metal within the sol-gel; it provides means for effectively controlling the porosity (pore-size and number of pores) and polarity (charge) of the sol-gel; and it enables coating of surfaces of virtually any shape, during gelation, such that a variety of sample holders, systems, and probes can be fabricated.

More particularly, certain objects of the invention are achieved by the provision of a method for producing a metal-doped sol-gel material, effective for surface-enhanced Raman spectroscopy, comprising the steps:

(a) providing a liquid formulation reactive for gelation to produce a sol-gel, the formulation comprising water; a matrix-forming component including a compound having the chemical formula $M(OR)_n$, wherein M is a metal selected from the group consisting of silicon, aluminum, titanium, zirconium, and mixtures thereof, R is an organic group, and n is of course an integer; ions of a SERS-active metal; and, optionally, a cosolvent for the water and the matrix-forming component;

(b) effecting gelation and drying of said formulation, at a temperature not in excess of 100° C., to produce a porous sol-gel material; and (c) treating at least one surface of said sol-gel material to effect reduction of said metal ions present at said surface to elemental-state particles.

It will be appreciated that gelation and drying (to remove water, with or without any residual organic solvent) may be effected as a continuous operation or as separate gelation and drying steps.

The matrix-forming component will preferably comprise a metal alkoxide, the organic group of which is a short alkyl chain, and the cosolvent employed will usually be a short chain (lower) alcohol. Preferably, the matrix-forming component will comprise tetramethylorthosilicate (TMOS), tetraethylorthosilicate (TEOS), or methyltrimethoxysilane (MTMS), and may desirably comprise a mixture thereof. In most instances the mole ratio of water to matrix-forming component will be in the range 0.01–50:1, and the mole ratio of cosolvent (when used) to water will be in the range 10–0.01:1.

The SERS-active metal ion will normally constitute about 0.1 to 15 mole percent of the formulation, and generally it will be of a Periodic Table Group IB metal. The metal ion will advantageously be introduced into the formulation as an aqueous solution of a complex, such as a silver amine complex. The elemental-state particles should have a diameter in the range 5 to 1000 nanometers and, when the ion is of a readily oxidizable metal, the step of gelation and drying will most desirably be carried out in an oxygen-starved atmosphere.

Other objects of the invention are attained by the provision of a method that includes the additional step of applying the liquid formulation to a substrate. Upon gelation, drying and reduction of the metal ion, the treated sol-gel material and substrate comprise a sensor for receiving, on at least the "one" surface, an analyte for Raman spectral analysis.

Additional objects are attained by the provision of a sensor produced by the method of the invention. Suitable substrates include slides, vials, multi-well micro-sample plates, tubes, optical elements (such as fiber optics, lenses, mirrors, and the like), and probe elements.

Further objects of the invention are attained by the provision of a method for carrying out surface-enhanced Raman spectral analysis of an analyte, comprising: providing the sol-gel material described; depositing an analyte upon the "one" surface of the sol-gel material; illuminating the one surface with radiation of at least one wavelength that is effective for causing the elemental-state particles to produce a plasmon field and for causing the field to interact with molecules of the analyte, to produce Raman photons; and collecting inelastically scattered radiation emitted from the one surface, for spectral analysis.

Still further objects are attained by the provision of Raman instrument comprising: a radiation source; a detector for detecting inelastically scattered radiation; a surface-enhanced Raman sensor produced in accordance herewith; and optics for directing radiation from the source upon the sensor, and for directing radiation emitted from the sensor upon the detector. The radiation source employed will usually produce radiation in the wavelength range of 250 to 2500 nanometers, and the elemental-state particle will have a diameter in the range 5 to 1000 nanometers; preferably, the particles will be of a Group IB metal.

DETAILED DESCRIPTION OF THE PREFERRED AND ILLUSTRATED EMBODIMENTS

As indicated above, the present invention provides a chemical synthesis route for incorporating metal particles within a sol-gel matrix, to produce a material that enables reproducible, reversible, and quantitative surface-enhanced Raman spectroscopic measurements to be made, in a highly efficient manner. Key components of the invention are: (1) the ability to control the porosity (pore size and number of pores) of the sol-gel material such that molecules readily flow into the sol-gel material and interact with the metal plasmom field, generally achieved through selection of specific ingredients (especially the metal alkoxide), concentrations, and processing conditions; (2) the ability to control the polarity of the sol-gel material to preferentially select which chemicals interact with the metal plasmon field, based primarily on chemical functional groups (e.g. acid versus base, and the length and functionality of the organic ligand of the metal alkoxide employed); and (3) the ability to control the size and concentration of the incorporated metal such that the efficiency of plasmon field generation, and hence of Raman scattering, is increased dramatically, desirably by a factor of one million or more (as compared to non-enhanced Raman scattering), generally by establishing optimal processing conditions, especially gelation and drying at low temperatures and in substantially oxygen-free environments.

Figure 1:
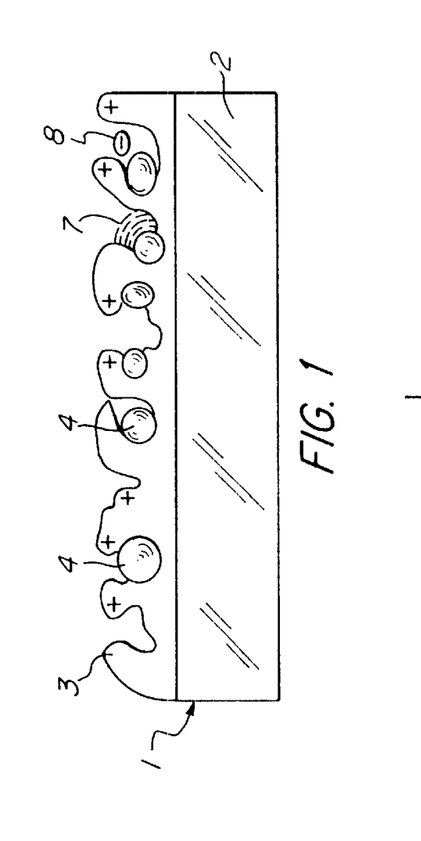
FIG. 1 is a diagrammatic representation of a sensor embodying the present invention, produced from a sol-gel containing metal particles and applied to a substrate.

FIG. 1 shows a cross-sectional view of a sensor, generally designated by the number 1, composed of a substrate 2 (e.g., a glass slide), coated with a sol-gel material 3 containing metal particles 4 and produced by the chemical synthesis route of the invention. The porosity of the sol-gel material, the polarity of the surface (indicated by plus signs), and the size of the metal particles are controlled by the choice of reactants, molar ratios, pH, and reaction rates (temperature), as will be described more fully below. The size of the metal particles is selected to optimize the generation of a plasmon field (suggested by the series of dashed curves at 7) when the metal particles are irradiated with a specific wavelength of light. The polarity of the sol-gel material is adjusted to selectively determine which molecules enter the pores, while the porosity is adjusted to optimize the flow of molecules (depicted by the encircled minus sign, at 8) to interact with the generated plasmon field 7. It will be appreciated that the polarities of the sol-gel material surface and the analyte molecules can of course be reversed from the foregoing indications.

The sol-gel process is a chemical route for the preparation of glasses and ceramics which are composed of group IA-IVA, IIIB and IVB metal oxides ($M_nO_m$), prime examples being $Si_nO_{2n}$, $Al_{2n}O_{3n}$, $Ti_nO_{2n}$, and $Zr_nO_{2n}$. Sol-gel glasses, ceramics, and other inorganic materials are normally prepared through the hydrolysis and condensation of an alkoxide ingredient having the general chemical formula: $M(OR)_n$, wherein R will typically be a lower ($C_1$–$C_4$) alkyl group and M represents one of the indicated metals, i.e., silicon aluminum, titanium, zirconium, and mixtures thereof; an exemplary metal-alkoxide is $Si(OCH_3)_4$, i.e., tetramethylorthosilicate (TMOS).

A detailed description of the sol-gel process is presented by E. M. Rabinovich, "Sol-Gel Processing, General Principles" in *Sol-Gel Optics: Processing and Applications*, L. C. Klein, Ed., Kluwer Acc. Pub., Chapter 1 (1994). The sol-gel process involves the preparation of a sol, i.e., a suspension of particles in a liquid (in the present method, a suspension of the metal-alkoxide in a suitable organic solvent is prepared), which undergoes a series of reactions including initial hydrolysis of the metal alkoxide followed by polycondensation to form a gel (i.e., a linked network of the particles). Expulsion of the solvent from the gel, by a drying process, results in a highly porous sol-gel material consisting of the metal oxides and any other additives that may have been introduced during the process. The chemical reactions (1) hydrolysis, (2) condensation, and (3) final condensation, respectively, can be represented as follows:

$M(OR)_n + xH_2O$ Metal alkoxide→$M(OH)_x(OR)_{n-x} + xROH$  (1)

$M(OH)_x(OR)_{n-x}$ Intermediate→$MO_{n/2} + (x/2)H_2O + ((n-x)/2)R_2O$  (2)

—M—(OH)+RO—M—→—M—O—M—+ROH gel  (3)

For $Si(OCH_3)_4$ the final gel will have primarily a silicate structure (—Si—O—Si—), which constitutes the backbone of a glass structure. The use of organoalkoxy silanes, such as TMOS, introduces the Si—C bond into the gel, in turn enabling several modifications to the final gel composition including the introduction of organic species or metal complexes as a part of the gel network structure. These can be further co-processed with cross-linking monomers, such as methyl methacrylate and its derivatives, urethanes, etc., to yield hybrid organic-inorganic gels.

The rates of hydrolysis and condensation are dependent primarily upon the characteristics of the reactants (e.g., the size of the alkyl ligand), the water content, and the pH of the sol (which may be acidic or basic depending, for example, upon the SERS-active metal compound employed). These parameters also govern the final structure of the gel. For instance, a low pH can be used to produce bulk sol-gel materials and thin films with ultrafine pores and a narrow pore-size distribution, while a high pH sol can be used to produce a fine powdery gel. The high level of chemical homogeneity and purity obtained has made the sol-gel process an extremely attractive option, as compared to conventional methods for the manufacture of ceramics and glasses. Furthermore, chemical compositions that may be unstable when produced at high temperatures are made possible simply by the addition of appropriate reactants to the formulation at any stage prior to initiation of the polycondensation-inorganic phases. Often, mixing at the atomic scale results in single-phase microstructures (in the classical sense), which are still hybrid mixtures of two components. Such materials are suitable for sensing applications and as catalytic supports. As will be discussed more fully below, the sol-gel materials can be fabricated in various forms, such as bulk monolithic gels, thin films, fibers and particulate substances.

Although silver is preferred, other metals known to be SER-active, especially copper and gold and less desirably nickel, palladium, and platinum (as well as alloys thereof), can also be incorporated into the sol-gel at suitable concentrations and so as to produce particles of suitable size in the sol-gel material. Generally, the metal particles will be incorporated into the sol-gel using a solvent selected to have a polarity that is effective to disperse the metal homogeneously throughout the formulation. For example, silver amine is suitably solvated by methanol and dispersed in a tetramethylorthosilicate solution. The choice of the SERS-active metal compound utilized can be used to control the size of the metal particles (coalescence of proximal particles), while the choice of solvent can influence the relative concentration of metal particles in the sol-gel material; the metal compound chosen may however limit the choice of effective solvents. The metal type and particle size will normally be so selected as to match a given excitation wavelength, for optimizing the generation of surface plasmons, and hence SER scattering.

More than one species of metal can be incorporated into the sol-gel if so desired. Metal alloys can be prepared (e.g. by underpotential electrochemical deposition) to have optical constants appropriate to the generation of surface plasmons, and can also be used. Again, each metal type may require a specific solvent or class of solvents. The metal complex or salt employed will also influence the rate of hydrolysis and condensation, and consequently the final structure and porosity of the sol-gel material. Nevertheless, these reaction rates can be controlled (e.g., by temperature adjustments) to ensure that the metal particle size distribution is relatively small, such that a plasmon field is generated in most of the metal particles. Control of the chemical process conditions also ensures a large number of pores and metal particles to increase the opportunity for the analyte to interact with the plasmon field.

Briefly stated, the selection of chemical reactants, their relative concentrations, and the reaction conditions (especially the solvent used, and the pH values and temperatures) allow control of the size and concentration of the metal particles and the sol-gel pore size.

In a paper by Y. H. Lee, S. Dai, and J. P. Young, entitled "Silver-doped sol-gel films as the substrate for surface-enhanced Raman scattering," *J. Raman Spectrosc.*, 28, 635–639 (1997), sol-gel synthesis procedures are described in which the previously developed silver-doped sol-gel is first dried in air for 30 minutes and then baked in an oven at 170° C. for 15 hours to promote condensation and sol-gel material formation. While being directly related to the method of the present invention, the technique described by Lee et al. is found to entail two significant deleterious preparation steps.

Firstly, gelation and/or drying in air promotes the formation of metal oxides (depending of course upon the particular metal involved), and such oxides are not adequately SER active. Secondly, the elevated temperature baking process disclosed promotes aggregation of the metal particles, which is most undesirable and reduces substantially the SER activity of the metal. In accordance with the synthesis process of the present invention, initial gelling desirably occurs in an oxygen-free or oxygen-starved environment (e.g., an atmosphere saturated with ethanol or an equivalent organic solvent), which prevents air oxidation of the metal, as is of course particularly important when one of the more reactive metals (e.g., silver) is involved.

Also, in accordance with the present invention condensation and sol-gel material formation are effected at temperatures ranging from about 20° to 100° C. Doing so minimizes aggregation of the metal particles and also promotes the formation of particles of optimal size. A highly effective SERS-active material is thus produced at practical rates and without need for the relatively high-temperature baking that characterizes prior art techniques.

Figure 9:
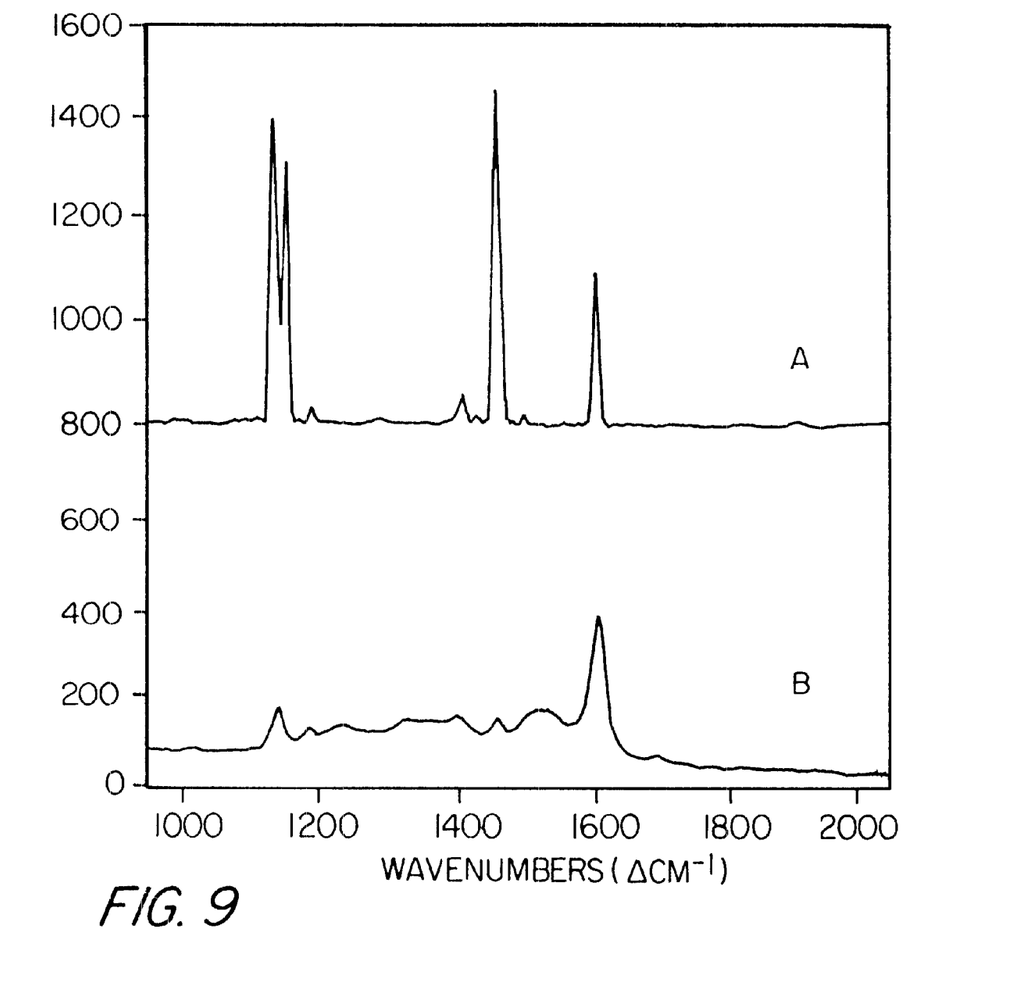
FIG. 9 is a plot of curves showing the SER spectra of p-aminobenzoic acid using silver-doped sol-gel material in which the silver is substantially (A) un-aggregated and (B) aggregated, respectively.

FIG. 9 of the drawings illustrates the foregoing principles. It shows SER spectra of p-aminobenzoic acid measured using (A) a sol-gel material of the invention, produced from a combined MTMS/TMOS formulation and heated, during gelation and drying, to a temperature less than 100° C., and (B) a sol-gel material produced using the same formulation from which however the MTMS is omitted and which is dried at a temperature above 120° C.; the scale of plot (B) is enlarged by a factor of 100, as compared to the scale of plot (A). In both instances a $10^{-3}$ molar PABA solution was used, and the test was performed using silver-doped sol-gel material-coated vials. The MTMS/TMOS sol-gel formulation consisted of the amine, methanol, TMOS and MTMS in a 1:4:2:2 volumetric ratio, and the MTMS-free formulation consisted of the amine, methanol, and TMOS in a 2:1:2 volumetric ratio.

As can be seen from curve A of FIG. 9, the MTMS/TMOS sol-gel material yields very intense, sharp spectral peaks, whereas the heated TMOS sol-gel material yields less intense, broad spectral peaks (curve B); indeed, the latter spectrum is nearly identical to a spectrum reported in the cited Lee et al. paper. The lower signal strength produces a level of measurement sensitivity that is correspondingly diminished, by two to three orders of magnitude, and the resultant loss of spectral resolution in turn greatly diminishes the ability to identify and distinguish chemicals, especially chemical mixtures, whereas it is a primary objective of the present invention to detect and identify trace chemicals. The reduction in signal intensity and resolution has been experimentally shown to be due to aggregation of the silver particles (see Laserna, J. J., A. Berthod, and J. D. Winefordner, "Evaluation and optimization of experimental conditions for surface-enhanced Raman detection of analytes in flow injection analysis," *Microchemical J.*, 38, 125–136 (1988)), and it is believed that aggregation caused by heating is responsible for the relatively low sensitivity evidenced by curve B of FIG. 9 (and of the Lee et al. spectrum).

Thus, the chemical synthesis described herein produces a SER-active material that is vastly superior to a similar material previously described in the literature. More particularly, an enhancement factor of more than $10^7$, as compared to $10^4$ enhancement cited in the literature, can for example be achieved for p-aminobenzoic acid. This is attributed to precise control of the particle size, porosity, and polarity afforded by the synthesis route provided by the present invention.

Figure 2:
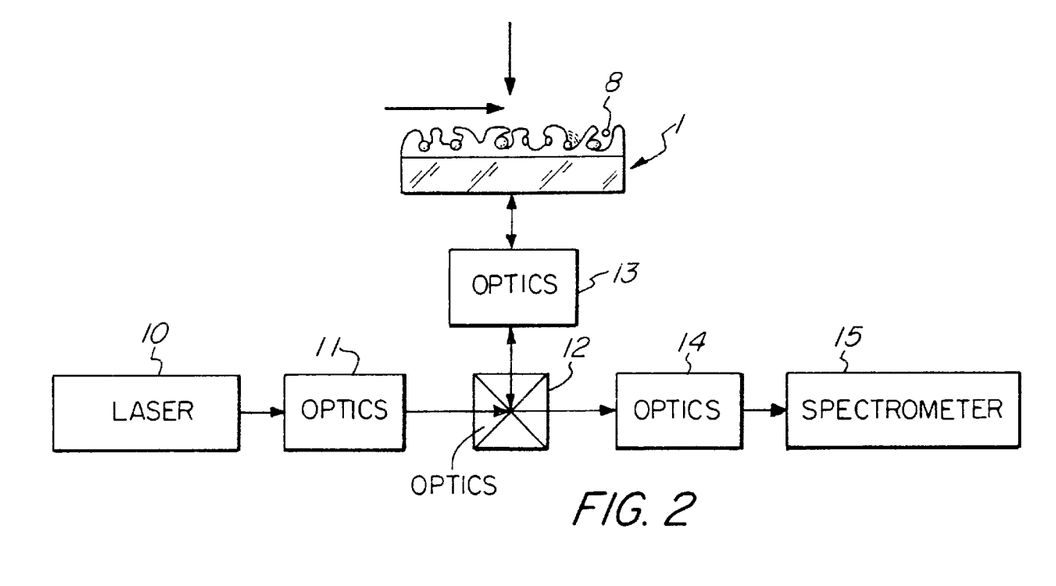
FIG. 2 is a block diagram schematically illustrating a Raman instrument embodying the present invention.

FIG. 2 diagrammatically illustrates apparatus suitable for use to measure the surface-enhanced Raman spectra of the molecules 8 introduced to the metal-doped sol-gel material sensor 1 by depositing the analyte upon the surface, or by flowing it thereacross, as depicted by the arrows. The apparatus consists of the following principal components: a laser source 10 to generate SER scattering in the sample, optics 11–14 to direct the laser beam to the sample and to collect the scattered radiation, and a Raman spectrometer 15 to separate the scattered light by wavelength or frequency to form a Raman spectrum. The wavelength of the monochromatic laser light will preferably be selected to match the optical constants of the metal particles, to thereby optimize the generation of a plasmon field. Pre-sample conditioning optics 11 are used to remove undesirable wavelengths of light, such as plasma lines. Optics 12, for directing the excitation light beam toward the sample, may employ, for example, a mirror, a prism, a fiber optic, an optical interference filter, or a notch filter, and further optics 13 may be used to maximize the illumination of the sample, the distribution of radiant energy, and the collection of the scattered radiation; such further optics may comprise, for example, a collimating lens, a cylindrical lens, a spherical lens, a combination of lenses (e.g., a microscope), a bifurcated fiber optic, or a combination of excitation and collection fiber optics. Such optics can be used to collect radiation reversely along the optical axis of excitation (back scattering), forwardly along the axis of excitation (forward scattering), or at an angle to the axis of excitation (side scattering). Post-sample conditioning optics 12 are used to remove undesired radiation, principally the elastically scattered (Rayleigh) radiation having a wavelength of light identical to the incident radiation, using interference or notch filters. Finally, optics 14, used to redirect the scattered radiation into the Raman instrument 15, may comprise a mirror, a prism, or a fiber optic, coupled with appropriate lenses to match the aperture of the Raman instrument. The Raman instrument 15 separates and disperses the light into its component wavelengths using a prism or grating, or into its component frequencies using an interferometer. A detector of the instrument 15 transforms the photon energy into electrical energy, such as by use of a photomultiplier tube, a photodiode (Si, Ge, or InGaAs), or a single or two-dimensional array of photodiodes (Si). The electrical energy is then used to produce a Raman spectrum, using means (not depicted) for displaying wavelength on the x-axis (usually in units of wavenumbers) and for displaying photon energy on the y-axis (usually in arbitrary units). This can be accomplished using a plotter or computer with appropriate hardware and software.

The method and apparatus of the invention may be employed as follows: a trace chemical in solution (e.g., a solution of one molecule of adenine per million molecules of water) is deposited dropwise on the metal-doped sol-gel material coated on a glass slide. The sensor 1 is illuminated from below by the excitation laser 10, the wavelength of which matches the metal particle size and optical constants so as to generate a plasmon field 7 in the metal particles 4. The plasmon field couples with nearby analyte molecules 8, thereby highly efficiently generating Raman photons. The Raman photons are collected, directed to the Raman instrument 15, and detected by its detector, being displayed, by the appropriate means referred to above, as a function of energy to produce a spectrum that is unique to the analyte; the spectrum identifies the analyte, whereas the band intensities quantify it (e.g., 1 ppm adenine).

Figure 4:
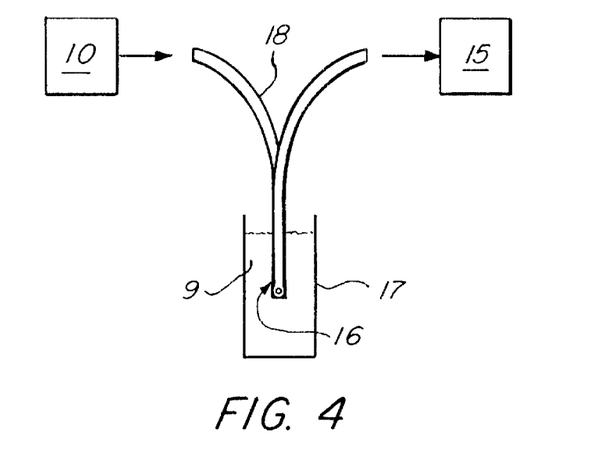
FIG. 4 is a diagrammatic representation of a sol-gel material-coated fiber optic tip probe embodying the present invention.
Figure 6A:
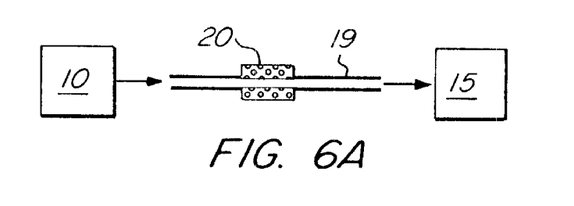
FIGS. 6A, 6B, and 6C are diagrammatic representations, of three forms of sol-gel material-clad fiber optics for SERS probes embodying the present invention.

As indicated by FIGS. 4, 6 and 7, and as will be described more fully below, the sample system can employ any of numerous forms of supports other than slides. Also, as shown by FIG. 7, the excitation and collection functions can occur from above or below, or at an angle or combination of angles relative to the support.

The following specific examples describe various configurations and applications in which the invention can be practiced:

EXAMPLE 1

Silver-doped Sol-gel Substrate for Trace Chemical Analysis

A silver-doped sol-gel material on a glass slide substrate, suitable for measuring trace chemicals by surface-enhanced Raman spectroscopy, is produced as follows: A silver amine complex ($Ag(NH_3)^{2+}$) is prepared from 30 weight percent ammonium hydroxide ($NH_3OH$) and 1 N silver nitrate ($AgNO_3$) in a 1:5v:v ratio. The amine complex is mixed at a 1:4:2:2 volumetric ratio to methanol ($CH_3OH$), tetramethylorthosilicate ($Si(OCH_3)_4$), and methyltrimethoxysilane (MTMS). The resulting liquid sol is then coated onto a glass slide, which is supported in a suitable fixture and rotated to produce a uniform coating. The coated slide is enclosed within a substantially air-tight container to provide an alcohol-saturated, oxygen-starved atmosphere, and mild heat (70° C.) is applied to speed expulsion of the solvent and formation of the sol-gel material; rotation and temperature allow thickness control. The silver cations ($Ag^+$) incorporated in the sol-gel material are then reduced to silver metal ($Ag°$) by soaking the gel with 0.1 M sodium borohydride ($NaBH_4$), after which residual sodium borohydride is neutralized and removed by washing with 0.1 M nitric acid ($HNO_3$).

A drop of a trace chemical dissolved in a suitable solvent ($10^{-6}$ mole of adenine in 1 mole of methanol) is then placed onto the activated surface of the doped sol-gel material of the prepared slide. A significant number of molecules of the target chemical are found to interact with the silver metal particles, through chemisorption, physisorption, or chemical reaction. A laser illuminates the substrate (20 scans, 8 $cm^{-1}$, 0.12 W, 1064 nm), generating surface-enhanced Raman scattering, which is collected by a Raman instrument. FIG. 3(C) shows the resulting Raman spectrum; FIG. 3(A) shows an infrared spectrum obtained by measuring a 300 mg KBr pellet containing 0.3 mg adenine, using 50 averaged scans, 4 $cm^{-1}$ resolution; and FIG. 3(B) shows the Raman spectrum of pure, solid adenine, 500 scans, 8 $cm^{-1}$, 0.4 W of 1064 nm laser radiation.

EXAMPLE 2

Figure 5:
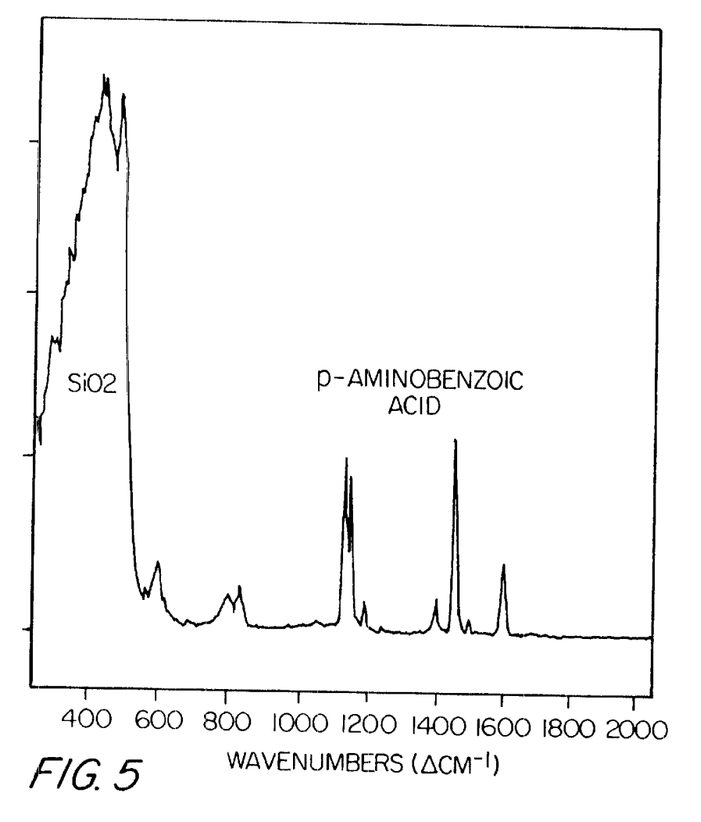
FIG. 5 is a plot showing the SER spectra of p-aminobenzoic acid (PABA), measured through the fiber tip probe of FIG. 4.

Silver-doped Sol-gel Coated on the Tip of a Fiber Optic for Trace Chemical Analysis The polished tip of an all silica fiber optic (silica cladding on a 600 μm diameter silica core) is dipped into a silver-doped sol-gel, which is then converted to a sol-gel material following which the silver is SER activated by reduction, as described in Example 1. The fiber withdrawal rate from the sol-gel solution and the temperature of the solution allow control of the sol-gel thickness on the fiber end-face. The resulting surface-enhanced fiber optic Raman sensor 16 is placed into a solution of the chemical 9, comprising molecules 8 to be detected, contained in a sample holder 17 (FIG. 4). A laser 10 illuminates the opposite end of the bifurcated fiber 18 (comprising a specific form of optics 13), which transmits the light to the coated fiber tip to thereby generate surface-enhanced Raman scattering. The SER scattering is transmitted back through the fiber and is directed into a Raman instrument 15. The forward (excitation) and backward (collected) light is separated by using the bifurcated fiber 18 (or, for example, an optical beam splitter). FIG. 5 shows the surface-enhanced Raman spectrum of p-aminobenzoic acid (PABA) measured at the tip of the sol-gel coated fiber sensor; the measurement conditions are 150 mW of 1064 nm excitation, 200 averaged scans, 8 cm$^{-1}$ resolution.

As will be appreciated, a fiber sensor can be incorporated into a number of forms of probes to enable sampling, such as a cone penetrometer used in analysis of chemical contaminants in subsurface water, or a syringe needle for monitoring drug metabolism intravenously.

EXAMPLE 3
Silver-doped Sol-gel as Fiber Optic Cladding for Chemical Analysis A section of the cladding is removed from a fiber optic 19 and replaced with an activated silver-doped sol-gel material coating 20 prepared as in Example 2, thereby forming a sensor that can then be placed into a solution containing the analyte. As is shown diagrammatically in FIG. 6A, a laser 10 illuminates one end of the fiber optic 19, which transmits the light to the coated fiber sensor region 20 to generate surface-enhanced Raman scattering. The SER scattering is transmitted along the fiber, passed through a filter (e.g., optics 12 of FIG. 2) to remove the laser wavelength from the spectrum, and directed into a Raman instrument 15.

Figure 6B:
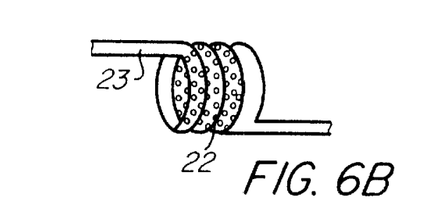
Figure 6C:
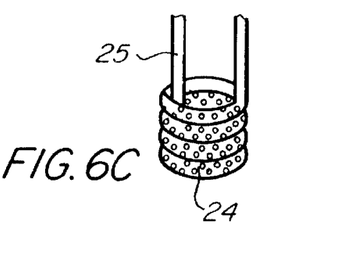

The fiber sensing region can be made into a number of shapes to enhance sampling, such as a coil 22 inside a flow tube sample system 23 or a coil 24 outside of a sample dipping rod 25 (FIGS. 6B and 6C).

Figure 7A:
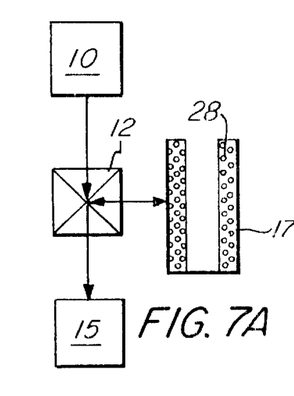
FIGS. 7A, 7B, 7C, and 7D are diagrammatic representations, respectively, of a sol-gel material-coated vial used in the back-scattering optical arrangement depicted, a sol-gel material-coated flow tube used in both transaxial and also axial scattering optical arrangements, and a sol-gel material-modified multiple-well micro-sample plate.
Figure 7B:
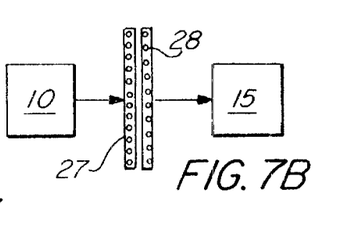

EXAMPLE 4
Silver-doped Sol-gel Coated Sample Tubes or Vials for Chemical Analysis With reference to FIG. 7A, silver-doped sol-gel solution, prepared as in Example 1, is poured into a glass vial or tube, such as sample holder 17. The vial or tube is rolled on its side to coat the inner wall to a desired gel thickness, as controlled by the roll speed and the temperature of the solution. The silver is then SER activated by reduction, as in Example 1, yielding a thin-film sensor comprised of the activated coating 28 on the inner wall.

A solution containing the chemical to be detected is then placed in the vial or flowed through the tube, as the case may be, and the beam of a laser 10 is directed through the wall to illuminate the sol-gel material coating and thereby generate surface-enhanced Raman scattering. The SER scattering is transmitted back through the sensor sidewall, collected, and directed into a Raman instrument 15. This forward (excitation) and backward (collected) light is separated using an optical beam splitter or a bifurcated fiber.

Figure 7C:
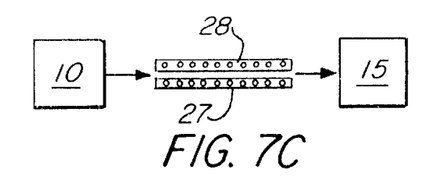

The tube 27 can be sufficiently small (e.g. 1 mm internal diameter) to enable excitation and collection of Raman scattering from the opposite sides, or transaxially (FIG. 7B), or in an on-axis configuration, as in a waveguide (FIG. 7C). It will be appreciated that flow sampling systems can also be composed of metal-doped sol-gel coated microchannels. Flow tube and microchannel probes can be used for example to detect chemicals separated in the mobile phase of a liquid chromatograph, whereas vials can be used conveniently in a multi-sample analysis device, such as carousel.

Figure 8:
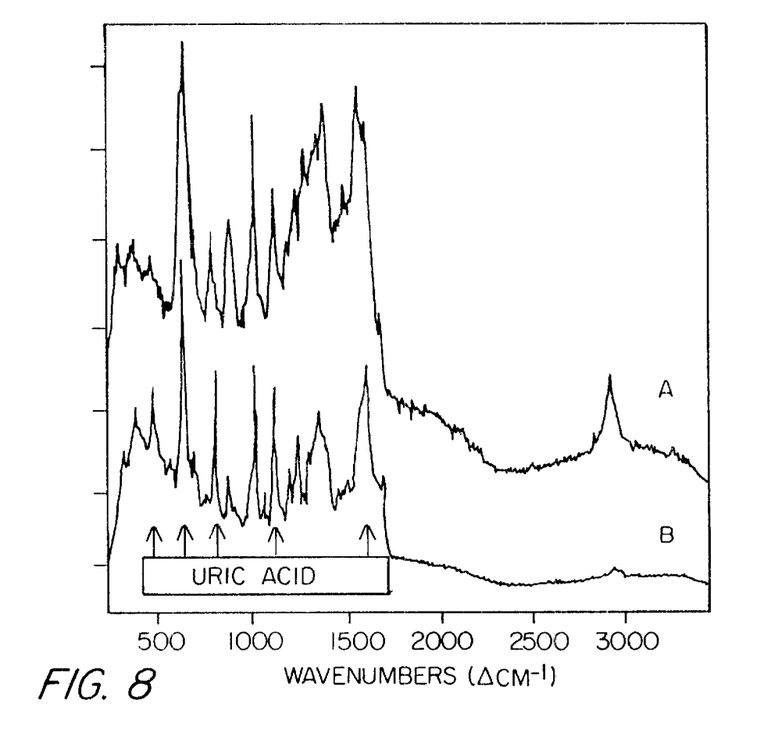
FIG. 8 is a plot of curves showing the SER spectra for each of two urine specimens using silver-doped sol-gel material-coated vials embodying the invention.

FIG. 8 shows the spectrum of uric acid detected in two urine specimens contained in a sol-gel coated glass vial. Both samples were at a pH of 6.5 and diluted to 50% strength with water; measurements were made at 120 mW, 1064 nm, 8 cm$^{-1}$, 50 scans; bands attributed to uric acid occur at 502, 650, 815, 1134, and 1616 cm$^{-1}$.

Figure 7D:
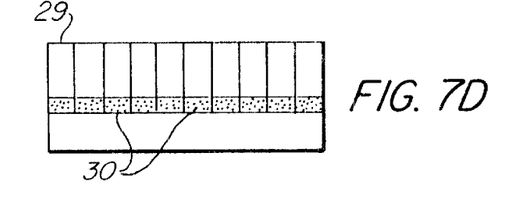

EXAMPLE 5
Silver-doped Sol-gel Coated Multi-compartment Plates for Chemical Analysis in Drug Discovery A silver-doped sol-gel solution, prepared as in Example 1, is added dropwise manually or automatically by a pipette or syringe to each compartment of a multi-well micro-sample plate 29, diagrammatically illustrated in FIG. 7D. The bottom surface of each well is coated to a desired gel thickness, as controlled by the drop size and the temperature of the solution and/or plate; a sol-gel material is produced, and the silver is SER activated by reduction, as in Example 1, yielding a thin-film sensor comprised of the activated coating 30 on the bottom surface of each well.

Various solutions containing chemicals to be detected are then placed in each well, and the beam of a laser 10 is directed through the bottom of each well (the plate being transparent to its radiation) to illuminate the sol-gel material coating and thereby generate surface-enhanced Raman scattering in a sequential fashion. The SER scattering is transmitted back through the bottom of the well, collected, and directed into a Raman instrument 15. This forward (excitation) and backward (collected) light is separated using suitable means. As will be appreciated, doped sol-gel material-coated micro-reactor plates could be used to analyze for target drugs in automated drug discovery.

It will also be appreciated that many variations can be made in the various features of the invention described without departing from the broad underlying concepts. Thus, the invention includes sol-gels doped with any appropriate SER-active metal or alloy, as identified above. For example, gold chlorohydrate (HAuCl$_4$●3H$_2$O) can be mixed with water and TMOS to produce a gold-doped sol-gel. Reduction of the metal can be effected other than by pure chemical means, such as electrochemical reduction (applied potential), photochemical reduction (ultraviolet irradiation), etc. In addition to TMOS, TEOS and MTMS, other organoalkoxy silanes, and combinations of such silanes, can be employed; alkoxide compounds of the form Si(OCH$_3$)$_3$(CH$_2$)$_n$R, which contain a functional organic group R with positive or negative charge, such as carboxylate or amine, can be utilized to select molecules to or screen molecules from the SER active site, based on polarity. Moreover, the invention contemplates using any suitable porous glass-forming metal oxide, such as Si$_n$O$_{2n}$, Al$_{2n}$O$_{3n}$, Ti$_n$O$_{2n}$, and Zr$_n$O$_{2n}$; it includes multi-glass component sol-gels (e.g. binary glasses: Si$_n$O$_{2n}$—Ti$_m$O$_{2m}$); it includes sol-gel material coated with a second layer to select molecules or to screen molecules from the SER-active sites; it includes sol-gel material coatings on a variety materials for the purpose of generating SERS, such as metals or plastics; it includes sol-gel material coatings on other optics, such as mirrors or lenses, for the purpose of generating SERS; it includes preparing fiber optic preforms consisting of either a metal-doped sol-gel interior or exterior, which can be melt-drawn to produce a metal-doped sol-gel material core or clad fiber optic; and it includes optical devices other than SERS chemical sensors, e.g., diffraction gratings or optical information storage devices produced by selective photoreduction of the metal (constructive and destructive interference pattern on a planar or curved sol-gel material surface), optical filters, or Raman optical shift generators produced by combining multiple metal-doped sol-gel layers. Although short-chain alcohols will often be most effective and practical for promoting the required hydration reaction in the sol-gel, chlorinated liquids such as carbon tetrachloride, methylene chloride, 1,1,1-trichloroethane and 1,1,2-trichloroethane, ketones such as acetone and methylethylketone, and other substances such as dimethyl sulfoxide and acetonitrile, may also be employed as cosolvents in the present system, as appropriate.

Thus, it can be seen that the present invention provides a novel method for preparing a SERS-active material that, in general, avoids the deficiencies of the techniques heretofore known, and that enables reproducible, reversible, and quantitative measurements to be performed with a high level of efficiency. It also provides a novel method for incorporating metal particles within a sol-gel material matrix so as to produce such a SERS-active material, and it provides a SERS-active material that is not restricted to specific environments, such as electrolytes, specific solvents, or as evaporates on surfaces, together with a method for the preparation thereof. The invention additionally provides novel sample holders (e.g., internally coated vials and multiple-well micro-sample plates), sampling systems (e.g., internally coated tubing for sample flow), optical elements (e.g., fiber optics, lenses and mirrors) and sample probes (e.g., externally coated rods or fiber optics that can be placed into a sample), suitable for use in performing SERS analyses. Furthermore, the invention provides a novel chemical analysis technique using surface-enhanced Raman spectroscopy and, in particular, such a technique that employs the sample holders, systems, optical elements and probes fabricated in accordance herewith.

Having thus described the invention what is claimed is:

1. A method for producing a metal-doped sol-gel material, effective for surface-enhanced Raman spectroscopy, comprising the steps:
   (a) providing a liquid formulation reactive for gelation to produce a sol-gel, said formulation comprising water; a matrix-forming component including a compound having the chemical formula $M(OR)_n$, wherein M is a metal selected from the group consisting of silicon, aluminum, titanium and zirconium, and mixtures thereof, and R is an organic group; and ions of a SERS-active metal;
   (b) effecting gelation and drying of said formulation, at a temperature not in excess of 100° C., to produce a porous sol-gel material; and
   (c) treating at least one surface of said sol-gel material to effect reduction of said metal ions present at said surface to elemental-state particles.

2. The method of claim 1 wherein said matrix-forming component comprises a metal alkoxide, said organic group being a short alkyl chain.

3. The method of claim 1 wherein said formulation additionally includes an organic cosolvent for said matrix-forming component and said water, and wherein said drying step additionally effects removal of residual cosolvent from the gelled formulation.

4. The method of claim 3 wherein said cosolvent is a short-chain alcohol.

5. The method of claim 1 wherein the mole ratio of said water to said matrix-forming component is in the range 0.01–50:1.

6. The method of claim 3 wherein the mole ratio of said water to said matrix-forming component is in the range 0.01–50:1, and wherein the mole ratio of said cosolvent to said water is in the range 10–0.01:1.

7. The method of claim 1 wherein said metal ion constitutes about 0.1 to 15 mole percent of said formulation.

8. The method of claim 7 wherein said metal ion is of a Group IB metal.

9. The method of claim 7 wherein said metal ion is introduced into said formulation as an aqueous solution of a complex of said metal ion.

10. The method of claim 9 wherein said complex is a silver amine complex.

11. The method of claim 1 wherein said elemental-state particles have a diameter in the range 5 to 1000 nanometers.

12. The method of claim 1 wherein said metal ion is of a readily oxidizable metal, and wherein said step of gelation and drying is carried out in an oxygen-starved atmosphere.

13. The method of claim 1 wherein said matrix-forming component comprises at least one compound selected from the group consisting of tetramethylorthosilicate, tetraethylorthosilicate, and methyltrimethoxysilane.

14. The method of claim 13 wherein said matrix-forming component comprises a mixture of at least two of said compounds.

15. The method of claim 1 including the additional step, effected intermediate said steps (a) and (b), of (d) applying said liquid formulation to a substrate, said treated sol-gel material and substrate comprising a sensor for receiving, on said at least one surface of said sol-gel material, an analyte for surface-enhanced Raman spectral analysis.

16. A metal-doped sol-gel material produced by the method of claim 1.

17. A sensor produced by the method of claim 15.

18. The sensor of claim 17 wherein said substrate is selected from the group consisting of slides, vials, multi-well micro-sample plates, tubes, optical elements, and probe elements.

19. A method for carrying out surface-enhanced Raman spectral analysis of an analyte, comprising:
   (a) providing said sol-gel material of claim 16;
   (b) bringing an analyte into effective contact with said at least one surface of said sol-gel material;
   (c) illuminating said at least one surface with radiation of at least one wavelength for causing said elemental-state particles to produce a plasmon field and for causing said field to interact with molecules of said analyte, in such effective contact, to produce Raman photons; and
   (d) collecting inelastically scattered radiation emitted from said one surface, for spectral analysis.

20. A Raman instrument, comprising:
   (a) a radiation source;
   (b) a detector for detecting inelastically scattered radiation;
   (c) a surface-enhanced Raman sensor; and
   (d) optics for directing radiation from said source upon said sensor, and for directing radiation emitted from said sensor upon said detector, said sensor comprising a sol-gel material produced by said method of claim 1.

21. The instrument of claim 20 wherein said radiation source produces radiation in the wavelength range of 250 to 2500 nanometers, and wherein said elemental-state particles have a diameter in the range 5 to 1000 nanometers.

22. The instrument of claim 21 wherein said particles are of a Group IB metal.

* * * * *